US006878125B1

(12) United States Patent
Bentivegna

(10) Patent No.: US 6,878,125 B1
(45) Date of Patent: Apr. 12, 2005

(54) INFLATABLE SUPPORT SHOE FOR A FOOT CAST

(76) Inventor: Robert Bentivegna, 1001 Longboat Ave., Beachwood, NJ (US) 08722

( * ) Notice: Subject to any disclaimer, the term of this patent is extended or adjusted under 35 U.S.C. 154(b) by 0 days.

(21) Appl. No.: 10/888,768

(22) Filed: Jul. 9, 2004

(51) Int. Cl.$^7$ .................................................. A61F 5/00
(52) U.S. Cl. .............................. 602/13; 602/23; 602/62; 128/DIG. 20; 128/882; 128/898; 2/DIG. 3
(58) Field of Search .............................. 602/13, 12, 23, 602/26, 27, 28, 29, 30, 62, 65, 66; 128/DIG. 20, 845, 118.1, 869, 882, 892, 893, 894, 898; 36/29, 153; 2/22, DIG. 3

(56) References Cited

U.S. PATENT DOCUMENTS

| | | | | | |
|---|---|---|---|---|---|
| 3,811,434 A | * | 5/1974 | Jacobson et al. | ............. | 602/13 |
| 4,628,945 A | * | 12/1986 | Johnson, Jr. | ................. | 602/27 |
| 5,363,632 A | * | 11/1994 | Armato | ........................ | 602/13 |
| 5,435,009 A | | 7/1995 | Schild | ............................. | 2/22 |
| 5,542,911 A | * | 8/1996 | Cassford et al. | .............. | 602/26 |
| 5,577,998 A | | 11/1996 | Johnson | ......................... | 602/5 |
| 5,626,557 A | * | 5/1997 | Mann | ........................... | 602/26 |
| 5,641,322 A | * | 6/1997 | Silver et al. | ................... | 602/13 |
| 5,792,084 A | * | 8/1998 | Wilson et al. | ................ | 602/13 |
| 5,957,872 A | | 9/1999 | Flick | ............................ | 602/13 |
| 6,256,787 B1 | * | 7/2001 | Tyler | ............................... | 2/22 |
| 6,511,449 B2 | * | 1/2003 | Burns et al. | ................... | 602/13 |
| 6,719,711 B1 | * | 4/2004 | Islava | ........................... | 602/13 |

* cited by examiner

Primary Examiner—Fadi H. Dahbour
(74) Attorney, Agent, or Firm—Goldstein Law Offices, P.C.

(57) ABSTRACT

An inflatable support shoe for enabling an individual with a broken foot encased within a cast to walk without the use of crutches. The support shoe comprises an inflatable footpad having a selectively inflatable air chamber, and a rubber ring. The footpad has a number of elastic cords extending therefrom having hooks at their ends. In use, the circular ring is selectively attached to the cast just above the ankle region of the cast. The user then positions the bottom of the cast upon the upper surface of the footpad, and engages the circular ring with the hooks at the ends of the cords, in order to firmly attach the footpad to the cast. After the user inflates the air chamber, the footpad cushions the injured foot against harmful impacts, thereby enabling the individual with a broken foot encased within a cast to walk upon the foot without the use of crutches.

7 Claims, 4 Drawing Sheets

INFLATABLE SUPPORT SHOE FOR A FOOT CAST

BACKGROUND OF THE INVENTION

1. Field of the Invention

The invention generally relates to a walking shoe, and in particular relates to an inflatable support shoe for a foot cast, for enabling an individual with a broken foot and a cast upon the foot to walk without the use of crutches.

2. Description of the Related Art

Thousands of individuals suffer from broken or fractured bones every year. Generally, the broken bone is set into proper alignment by a physician, and the injured area is then encased within a cast. Casts hold the broken bone(s) in place as they heal in order to ensure that they heal properly. Casts are typically constructed from a non-resilient material such as plaster, and do little to cushion the injured foot against harmful impacts. A pair of walking crutches is usually provided to an individual with a broken foot so that he/she will be able to walk without exerting undue pressure on the injured foot. However, there are notable disadvantages associated with using crutches while walking with a broken foot encased within a cast. In particular, crutches are unwieldy and hard for the user to operate and maneuver. What's more, use of crutches is generally uncomfortable, and the crutches often exert painful pressure upon the underarm areas of the user. Accordingly, there is a need for an inflatable support shoe that is designed to selectively fit onto a foot cast, and which cushions the user's foot against impacts with the ground while walking, thereby enabling an individual with a broken foot encased within a cast to walk without exerting undue pressure upon the broken foot, and without using uncomfortable and unwieldy crutches.

A variety of inflatable footwear has been devised. For example, U.S. Pat. No. 5,577,998 to Johnson, Jr. appears to show a walking brace used in conjunction with an existing cast, having inflatable air cells for bearing the weight of a user. Additionally, U.S. Pat. No. 5,957,872 to Flick appears to show a heel care device having an inflatable member for providing protection for, and for relieving pressure on the heel area of the foot. Furthermore, U.S. Pat. No. 5,435,009 to Schild appears to show an inflatable compression garment for an injured limb for treating vascular disorders and for alleviating swelling.

While these devices may be suitable for the particular purpose employed, or for general use, they would not be as suitable for the purposes of the present invention as disclosed hereafter.

SUMMARY OF THE INVENTION

It is an object of the invention to provide an inflatable support shoe for a foot cast that enables an individual with a broken foot and a cast upon the foot to walk without the use of crutches. Accordingly, the support shoe comprises an inflatable footpad having a selectively inflatable air chamber. After the individual selectively inflates the air chamber with an existing supply of pressurized air and attaches the footpad to the cast, the footpad cushions the foot against harmful impacts, thereby enabling the individual to walk without the use of crutches.

It is another object of the invention to provide an inflatable support shoe that is selectively and easily attachable onto a foot cast. Accordingly, the inflatable support shoe further comprises a stretchable circular ring that is selectively attached to the cast just above the ankle region of the cast. The footpad has a number of stretchable cords extending therefrom having hooks for selectively engaging the circular ring, thereby providing an inflatable support shoe that is selectively and easily attachable onto a foot cast.

It is yet another object of the invention to provide an inflatable support shoe that is not unduly expensive. Accordingly, the materials from which the inflatable support shoe is constructed are readily available, and its cost is not prohibitive.

Further objects of the invention will become apparent in the detailed description of the invention that follows.

The invention is an inflatable support shoe for enabling an individual with a broken foot encased within a cast to walk without the use of crutches. The support shoe comprises an inflatable footpad having a selectively inflatable air chamber, and a rubber ring. The footpad has a number of elastic cords extending therefrom having hooks at their ends. In use, the circular ring is selectively attached to the cast just above the ankle region of the cast. The user then positions the bottom of the cast upon the upper surface of the footpad, and engages the circular ring with the hooks at the ends of the cords, in order to firmly attach the footpad to the cast. After the user inflates the air chamber, the footpad cushions the injured foot against harmful impacts, thereby enabling the individual with a broken foot encased within a cast to walk upon the foot without the use of crutches.

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are depicted by like reference numerals. The drawings are briefly described as follows.

DETAILED DESCRIPTION OF THE PREFERRED EMBODIMENTS

Figure 1:
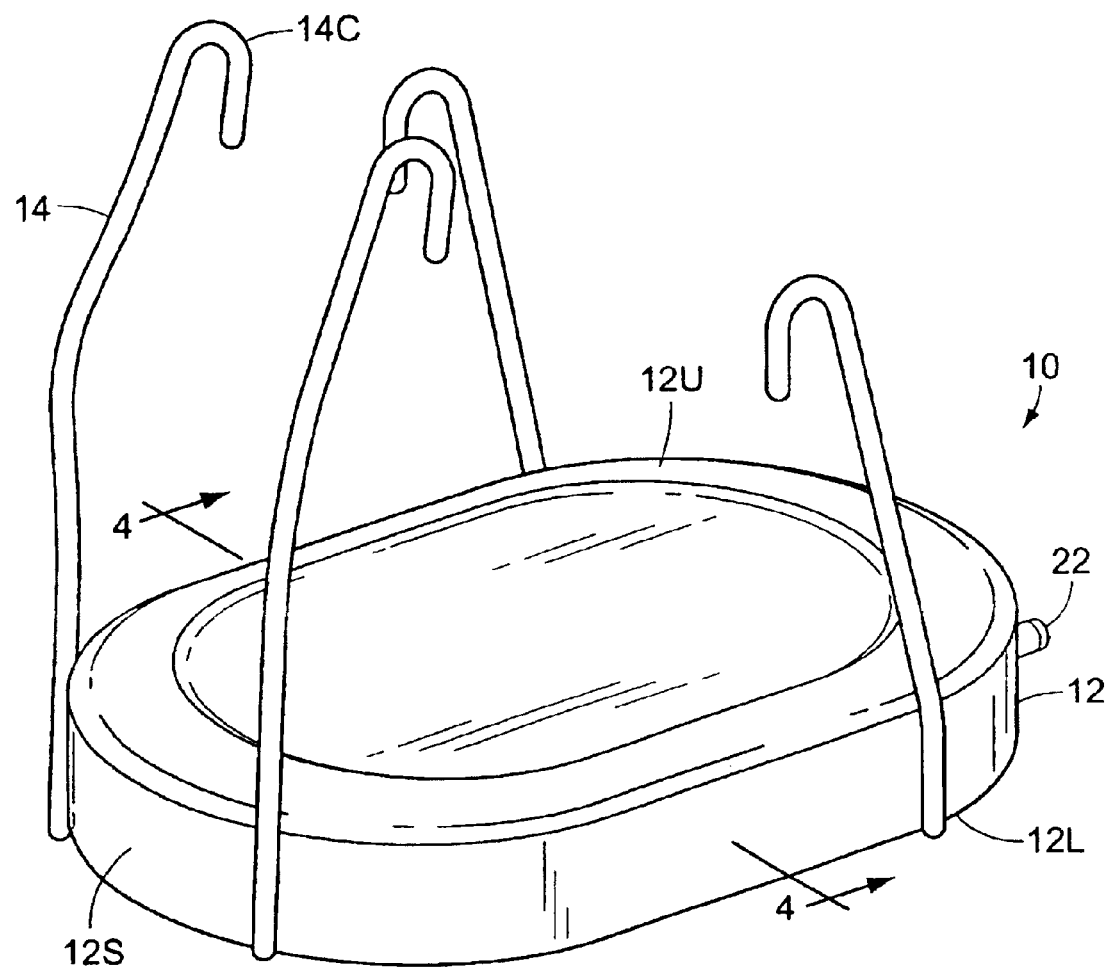
FIG. 1 is a perspective view of an inflatable footpad of an inflatable support shoe according to the present invention.

FIG. 1 illustrates an inflatable footpad 12 of an inflatable support shoe 10 according to the present invention. The support shoe 10 additionally comprises a stretchable circular ring 16, which will be described with reference to FIG. 2 and FIG. 3. The inflatable support shoe 10 enables an individual with a broken foot and a cast upon the foot to walk without the use of crutches, as will be described.

Figure 4:
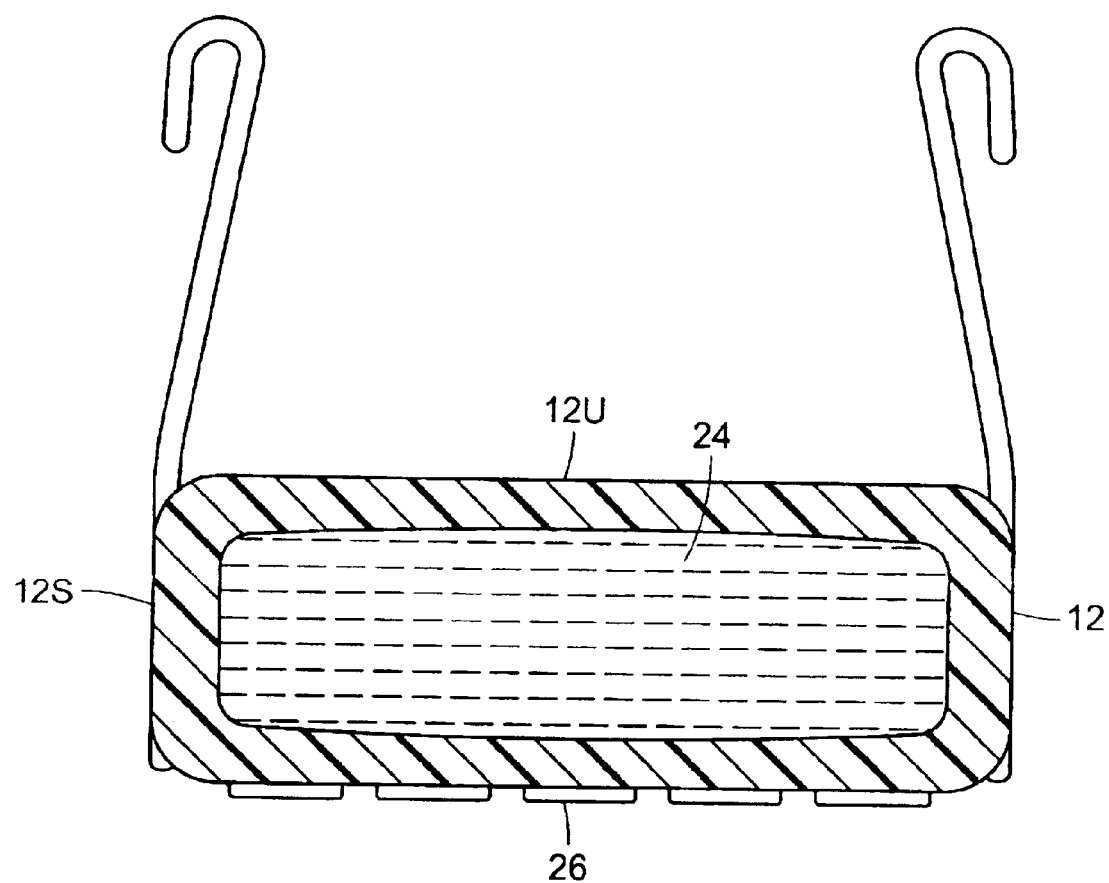
FIG. 4 is a cross-sectional view of the inflatable footpad, illustrating an air chamber contained therein.

The footpad 12 has an upper surface 12U, a lower surface 12L, and sides 12S, and has an air valve 22 extending from one of the sides 12S. The footpad 12 contains an air chamber 24 that is in communication with the air valve 22. The air chamber 24 may be seen in the cross-sectional view of FIG. 4. A user of the inflatable support shoe 10 selectively inflates the air chamber 24 by connecting the air valve 22 to an existing supply of pressurized air. The inflatable footpad 12 cushions the injured foot against harmful impacts, thereby enabling the user with a broken foot and a cast upon the foot to walk without the use of crutches. The footpad 12 has a number of stretchable cords 14 extending therefrom. Each cord 14 has a hook 14C at its end for selectively engaging the circular ring 16.

Figure 2:
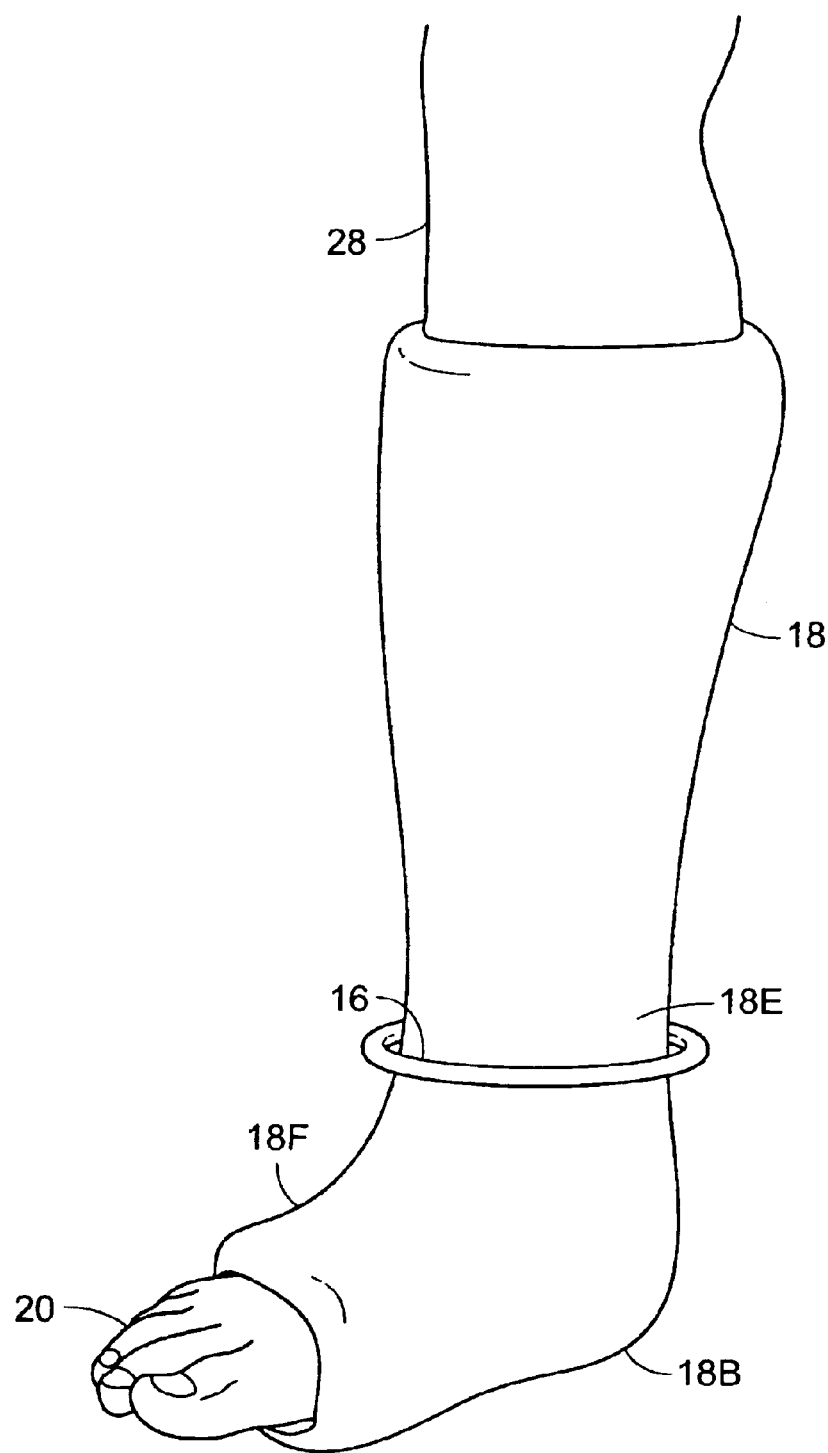
FIG. 2 is a perspective view of a leg and a foot substantially encased within a cast, wherein a stretchable ring of the inflatable support shoe selectively encircles the ankle region of the cast.

FIG. 2 illustrates a leg 28 and a foot 20 of an individual wearing a cast 18. The lower portion of the leg 28 and the foot 20 are substantially encased within the cast 18. The cast 18 has a foot portion 18F, an ankle region 18E, and a bottom 18B. The user has extended the foot portion 18F of the cast 18 concentrically through the circular ring 16 and has positioned the circular ring 16 around the ankle region 18E of the cast 18.

Figure 3:
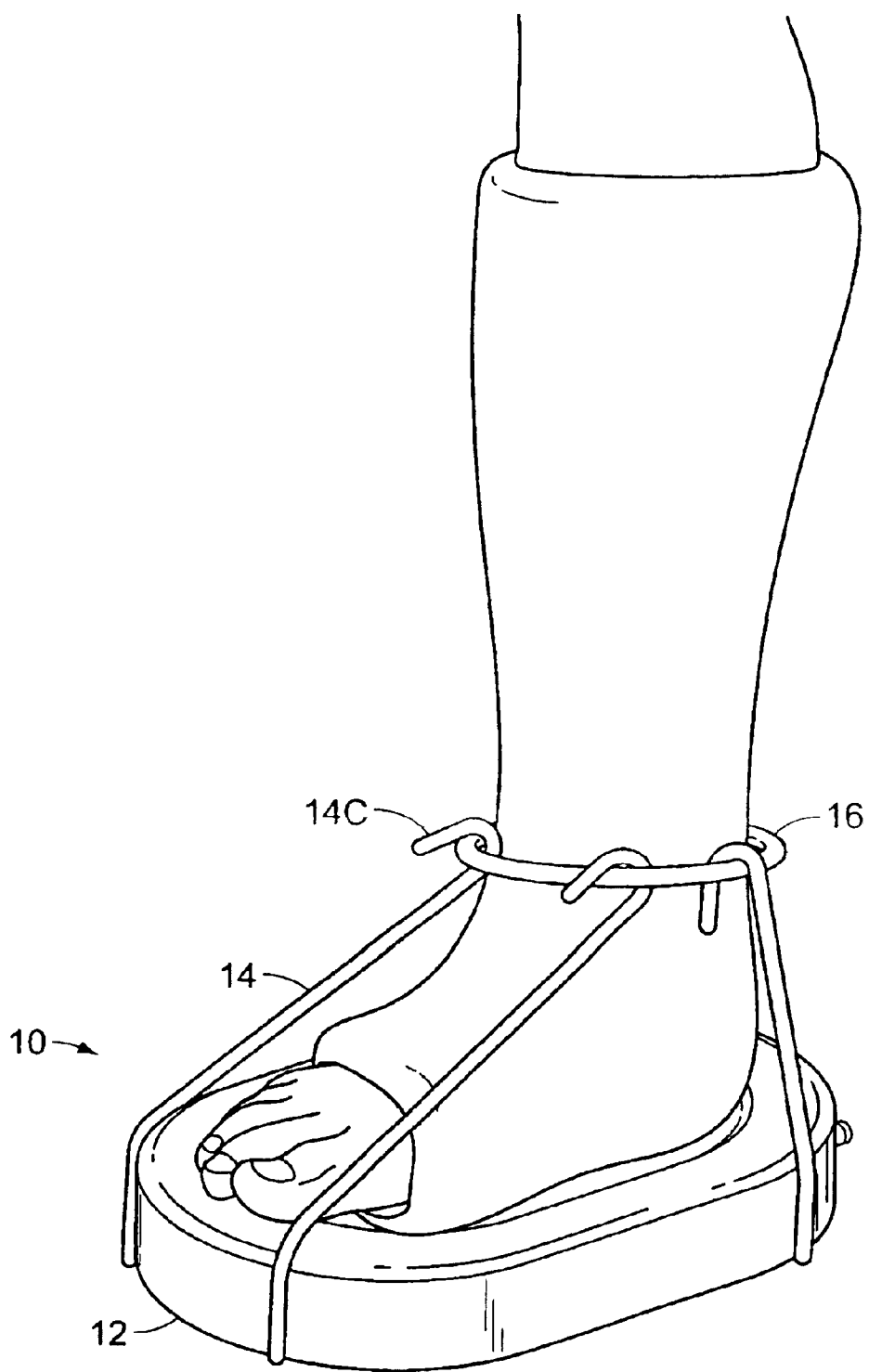
FIG. 3 is a perspective view as in FIG. 2, except that the inflatable footpad has been positioned underneath the cast, and cords extending from the inflatable footpad have been used to engage the stretchable ring in order to secure the footpad to the cast.

FIG. 3 is a view as in FIG. 2, except that the user has positioned the bottom 18B of the cast 18 upon the upper surface 12U of the footpad 12, and has engaged the circular ring 16 with the hooks 14C at the ends of the cords 14, in order to firmly attach the footpad 12 to the cast 18.

The footpad 12 is preferably constructed from a durable rubber. Returning momentarily to FIG. 4, the lower surface 12L of the footpad 12 has treads 26 for providing traction so that the footpad 12 will not slip on a floor while being deployed. The treads 26 are preferably constructed from rubber. The stretchable cords 14 are preferably constructed from elastic, but a different strong stretchable material may be substituted for the elastic. The circular ring 16 is preferably constructed from rubber, but a different strong stretchable material may be substituted for the rubber. The inflatable support shoe 10 is provided in a number of sizes so that it may be suitably used in conjunction with differently sized casts 18.

In use, a user of the inflatable support shoe 10 inflates the air chamber 24 of the footpad 12 by connecting the air valve 22 to a source of pressurized air and by turning on the supply of air. The user extends the foot portion 18F of the cast 18 concentrically through the circular ring 16 and positions the circular ring 16 around the ankle region 18E of the cast 18. The user positions the lower surface 12L of the footpad 12 upon an existing horizontal support structure such as a floor, and places the bottom 18B of the cast 18 upon the upper surface 12U of the footpad 12. The user secures the footpad 12 to the circular ring 16 with the hooks 14C at the end of each of the cords 14. The user is then able to walk without the use of crutches because the inflatable footpad 12 cushions the injured foot against harmful impacts with the floor. For feet that are severely injured, the user may use a walking cane to lessen the amount of pressure applied to the injured foot while walking. After use, the footpad 12 is detached from the circular ring 16, and the circular ring 16 is removed from the cast 18. The inflatable support shoe 10 may be compactly stored between successive uses.

In conclusion, herein is presented an inflatable support shoe for a foot cast, for enabling an individual with a broken foot and a cast upon the foot to walk without the use of crutches. The invention is illustrated by example in the drawing figures, and throughout the written description. It should be understood that numerous variations are possible, while adhering to the inventive concept. Such variations are contemplated as being a part of the present invention.

What is claimed is:

1. An inflatable support shoe for a foot cast, for use in conjunction with an existing supply of pressurized air, for enabling a user with a broken foot and a cast upon the foot to walk without the use of crutches, said cast having an ankle region and a bottom, comprising:
   a stretchable circular ring;
   an inflatable footpad for selectively cushioning the broken foot against harmful impacts, said footpad having:
      an upper surface, a lower surface, and sides;
      an air valve extending from one of the sides;
      an air chamber contained within the footpad and in communication with the air valve, wherein the user selectively inflates the air chamber by connecting the air valve to the existing supply of pressurized air; and
      a plurality of stretchable cords extending therefrom, each having a hook for selectively engaging the circular ring; and
   wherein during use, the user extends the foot portion of the cast concentrically through the circular ring, positions the circular ring around the ankle region of the cast, positions the bottom of the cast upon the upper surface of the footpad, and uses the hooks of the cords extending from the inflatable footpad to engage the circular ring in order to secure the footpad to the cast.

2. The inflatable support shoe as recited in claim 1, wherein the lower surface of the footpad has treads for providing traction so that the footpad will not slip while being deployed.

3. The inflatable support shoe as recited in claim 2, wherein the treads are constructed from rubber.

4. The inflatable support shoe as recited in claim 3, wherein the footpad is constructed from rubber.

5. The inflatable support shoe as recited in claim 4, wherein the circular ring is constructed from rubber.

6. The inflatable support shoe as recited in claim 5, wherein the cords are substantially constructed from elastic.

7. A method for enabling a user with a broken foot and a cast upon the foot to walk upon an existing horizontal support structure without the use of crutches, said cast having a foot portion, an ankle region, and a bottom, said method utilizing an inflatable support shoe having a stretchable circular ring and an inflatable footpad, said footpad having an upper surface, a lower surface, and sides, an air valve extending from one of the sides, an air chamber contained within the footpad, and in communication with the air valve, and a plurality of stretchable cords extending therefrom, each having a hook, said method utilizing an existing supply of pressurized air, said method comprising the steps of:
   inflating the air chamber of the footpad by the user by connecting the air valve to the source of pressurized air and by turning on the supply of air;
   extending the foot portion of the cast concentrically through the circular ring and positioning the circular ring around the ankle region of the cast;
   positioning the lower surface of the footpad upon the existing horizontal support structure;
   placing the bottom of the cast upon the upper surface of the footpad;
   securing the footpad to the circular ring with the hook at the end of each of the cords;
   walking without the use of crutches because the inflatable footpad cushions the broken foot against harmful impacts with the horizontal support structure;
   detaching the footpad from the circular ring and removing the circular ring from the cast; and
   storing the inflatable support shoe between successive uses.

* * * * *